US009603792B2

(12) United States Patent
John (10) Patent No.: US 9,603,792 B2
(45) Date of Patent: *Mar. 28, 2017

(54) SYSTEM AND METHOD FOR CORRECTION OF INTRACEREBRAL CHEMICAL IMBALANCES

(71) Applicants: New York University, New York, NY (US); Leslie S. Prichep, Mamaroneck, NY (US)

(72) Inventor: Erwin R. John, Mamaroneck, NY (US)

(73) Assignee: New York University, New York, NY (US)

(*) Notice: Subject to any disclaimer, the term of this patent is extended or adjusted under 35 U.S.C. 154(b) by 602 days.

This patent is subject to a terminal disclaimer.

(21) Appl. No.: 14/160,022

(22) Filed: Jan. 21, 2014

(65) Prior Publication Data

US 2014/0135743 A1    May 15, 2014

Related U.S. Application Data

(63) Continuation of application No. 13/555,533, filed on Jul. 23, 2012, now Pat. No. 8,647,329, which is a (Continued)

(51) Int. Cl.
*A61M 27/00* (2006.01)
*A61K 9/00* (2006.01)
(Continued)

(52) U.S. Cl.
CPC ............ *A61K 9/0004* (2013.01); *A61B 5/031* (2013.01); *A61B 5/0476* (2013.01); *A61M 27/006* (2013.01)

(58) Field of Classification Search
CPC .. A61M 5/1407; A61M 5/1408; A61M 5/142; A61M 5/14593; A61B 5/031; A61B 5/3476

See application file for complete search history.

(56) References Cited

U.S. PATENT DOCUMENTS 4,915,688 A * 4/1990 Bischof .................. A61J 3/002
137/606
5,798,114 A * 8/1998 Elsberry .............. A61K 9/0024
424/423

(Continued)

*Primary Examiner* — Laura Bouchelle
(74) *Attorney, Agent, or Firm* — Fay Kaplun & Marcin, LLP (57) ABSTRACT

A method of treating a central nervous system (CNS) disorder, comprises the steps of inserting into a patient's body first and second conduits so that distal ends of the first and second conduits open to a portion of the patient's CNS with direct access to cerebrospinal fluid (CSF) and a proximal end of the first conduit opens into a first reservoir of material to be introduced into the CSF and a proximal end of the second conduit opens to drain CSF withdrawn from the CNS in combination with the steps of detecting and analyzing brain activity of a patient and determining a chemical imbalance present in the CSF by one of a microassay of a sample of CSF withdrawn from the second reservoir and the detected and analyzed brain activity. Based on the determined chemical imbalance, the patient is treated by one of supplying an agent to the CSF via the first conduit and withdrawing a quantity CSF via the second conduit. A system for treating disorders of the central nervous system (CNS), comprises first and second conduits, wherein, when in an operative position, distal ends of the first and second conduits open into a portion of a patient's CNS with direct access to cerebrospinal fluid (CSF) and wherein, when in the operative position, a proximal end of the second conduit opens to drain CSF from the CNS and a first reservoir implantable within the patient's body and holding material to be introduced to the CNS in combination with a first pump coupled to the first reservoir and the first conduit for introducing the material to the CNS via the first conduit and a brain wave detection unit for detecting and analyzing brain waves of the patient.

19 Claims, 4 Drawing Sheets

Related U.S. Application Data continuation of application No. 12/748,826, filed on Mar. 29, 2010, now Pat. No. 8,226,594, which is a continuation of application No. 10/672,100, filed on Sep. 26, 2003, now Pat. No. 7,686,780.

(51) Int. Cl.
  *A61B 5/03* (2006.01)
  *A61B 5/0476* (2006.01)

(56) References Cited

U.S. PATENT DOCUMENTS

| | | | | |
|---|---|---|---|---|
| 6,471,688 B1 * | 10/2002 | Harper | ............... | A61M 5/14276 424/424 |
| 8,647,329 B2 * | 2/2014 | John | ..................... | A61B 5/031 604/891.1 |

* cited by examiner

SYSTEM AND METHOD FOR CORRECTION OF INTRACEREBRAL CHEMICAL IMBALANCES

This application is a Continuation application of U.S. patent application Ser. No. 13/555,533 filed on Jul. 23, 2012, now U.S. Pat. No. 8,647,329; which is a Continuation of U.S. patent application Ser. No. 12/748,826 filed on Mar. 29, 2010, now U.S. Pat. No. 8,226,594; which is a Continuation application of U.S. patent application Ser. No. 10/672,100 filed on Sep. 26, 2003, now U.S. Pat. No. 7,686,780. The entire disclosures of the prior patents/applications are considered as being part of the disclosure of the accompanying application and hereby expressly incorporated by reference herein.

BACKGROUND INFORMATION

The present invention relates generally to a system and method for treating conditions of the brain. More specifically, the present invention relates to a catheter assembly and method for intraventricular shunting and lavage for the change of neurophysiological imbalances in the central nervous system (CNS).

Apoprotein and other substances accumulate in the brain tissues of patients suffering from cognitive imp ailment associated with aging (e.g., Alzheimer's disease). Patients in a coma after traumatic head injury, patients suffering from dementia, and patients with a variety of other psychiatric disorders are also known to display imbalances or deficiencies of a variety of cerebral neurotransmitters and electrolytes.

Patients in a coma after traumatic head injury are known to display several kinds of neurophysiological disequilibria, for example, excessively high intracranial pressure which may depress the regulation of vital functions or create deficits of neurotransmitters such as Acetylcholine or serotonin resulting in a diminution of activating and arousal processes.

Precursors and metabolites of neurotransmitters are also present in the cerebrospinal fluid (CSF) which establishes an equilibrium by diffusion with the extracellular fluid (ECF) which is the intimate environment of the parenchyma tissue, neurons and glia. The CSF concentrations of these substances may provide clinically useful information about excesses or deficits of neurotransmitters in the tissue.

Such neurophysiological disequilibria may result in a build up of toxic substances in the CSF. Excessive amounts of metabolite produced in one brain region may diffuse via the CSF to other regions where they may alter the balance of reversible reactions. Intracranial pressure (ICP) may increase, causing depression of centers in the brainstem that are essential for maintenance and regulation of vital functions. Such alterations of normal ICP are encountered in clinical conditions such as hydrocephalus or traumatic brain injury. The CSF may be drained from the CSF space to adjust the ICP, and the concentrations of metabolites or precursors of critical substances may be subjected to microassay outside the cranium.

The removal of CSF to treat Alzheimer's disease, hydrocephalus, brain edema, or other diseases may be accomplished by the use of a variety of intracranial devices, as is known in the art. To remove these undesirable toxic substances or correct these undesirable pressures, a drainage device such as a shunt or a catheter may be placed in a ventricle of the brain.

SUMMARY OF THE INVENTION

The present invention is directed to a method of treating a central nervous system (CNS) disorder, comprising the steps of inserting into a patient's body first and second conduits so that distal ends of the first and second conduits open to a portion of the patient's CNS with direct access to cerebrospinal fluid (CSF) and so that a proximal end of the first conduit opens into a first reservoir of material to be introduced into the CSF and a proximal end of the second conduit opens to drain CSF withdrawn from the CNS and detecting and analyzing brain activity of a patient in combination with the steps of determining a chemical imbalance present in the CSF by one of a micro assay of a sample of CSF withdrawn from the second reservoir and the detected and analyzed brain activity and treating the patient based on the determined chemical imbalance by one of supplying an agent to the CSF via the first conduit and withdrawing a quantity CSF via the second conduit.

The present invention is further directed to a system for treating disorders of the central nervous system, comprising first and second conduits, wherein, when in an operative position, distal ends of the first and second conduits open into a portion of a patient's CNS with direct access to cerebrospinal fluid and wherein, when in the operative position, a proximal end of the second conduit opens to drain CSF from the CNS and at least one reservoir implantable within the patient's body and holding material to be introduced to the CNS in combination with a first pump coupled to the first reservoir and the first conduit for introducing the material to the CNS via the first conduit and a brain wave detection unit for detecting and analyzing brain waves of the patient.

DETAILED DESCRIPTION

Those skilled in the art will understand that it may, at times, be desirable to administer pharmacotherapeutic drugs or other therapeutic agents to treat chemical imbalances in the brain. However, the effective availability of many of the pharmacotherapeutic drugs administered to treat such is limited by their inability to cross the blood-brain barrier ("BBB"). Further, although precursors, agonists and antagonists of these substances are well known, the ability to deliver effective cerebral doses is sometimes seriously constrained by their possible systemic side effects.

Those skilled in the art will understand that it may, at times, be desirable to adjust the ICP by removing CSF or by adding synthetic artificial CSF to optimize pressure dependent homeostatic functions.

The invention enables aggressive intervention in brain disorders by adaptively correcting the contribution of a suboptimal fluid environment to the health of neural tissue, adjusting ICP or otherwise restoring an optimal extracellular neurochemical balance by circumventing the brain's resistance to drug entry posed by the BBB, as well as possible systemic side effects, by a direct delivery into the CSF using a minimally invasive technology coupled with bioassay and electrophysiological monitoring techniques.

The CSF surrounding the brain and spine is naturally produced in the chorioid plexus in the ventricles and reabsorbed by arachnoid villi. Swelling of the brain due to edema caused by concussion commonly causes blockage of reabsorption pathways resulting in a pathological increase in ICP. Similar dangerous excesses of ICP and disturbances of brain development can be caused by blockage of the cerebral ventricles in hydrocephalus. It is believed that certain brain disorders such as, for example, Alzheimer's disease, may result from the presence of certain toxic substances in the CSF. These toxins may, for example, be generated by diseased neurons at a rate greater than the rate at which they are removed by regeneration of the CSF, resulting in an accumulation of toxins, in the CSF. Known toxic substances include beta A-4 amyloid, beta-2 microglobulin, tau, etc. Other conditions are known to cause increases or decreases in the availability of neurotransmitters or their precursors.

The ECF which is the intimate environment of the brain cells is in reversible diffusion exchange with the CSF and therefore conveys neurotransmitters and their precursors and metabolites from various brain regions into the CSF.

As would be understood by those skilled in the art, the power spectrum of the EEG is regulated by a homeostatic neuro anatomical system in the brain which is dependent upon appropriate availability of neurotransmitters. Excesses or deficits of these substances perturb this regulation. Therefore, quantitative analysis of the EEG can serve as an indicator of neurotransmitter availability.

As would be understood by those skilled in the art, increases in ICP following traumatic brain injury or other conditions may result in swelling of the brain and increases in the ICP that can have serious consequences including death, and are a subject of great concern in the trauma intensive care unit.

The present invention is directed to a system and method for correcting such imbalances. In one embodiment of the invention, the system may be automated to maintain a desired chemical balance in the CSF using dynamic feedback from EEG monitoring and periodic chemical analysis of the CSF. However, a more basic system according to the present invention may include, for example, a shunting catheter for shunting CSF from the cranium and an infusion catheter for infusing necessary chemicals (i.e., electrolytes, agonists, antagonists, etc.) into the cranium via an osmotic pump, while monitoring and regulating the effects of the intraventricular shunting and lavage with periodic quantitative electroencephalographic (QEEG) assays and with chemical analysis of the shunted CSF performed by clinical personnel.

In one embodiment of the invention, the system may be automated to maintain a desired ICP using dynamic feedback from a sensor monitoring the ICP to regulate the outflow of CSF from the shunt. For example, an indwelling pressure sensor may periodically detect ICP and forward this data to a processor so that, when an ICP value outside an acceptable range is detected, external personnel may be notified or automatic control of a pump to add or withdraw CSF may be undertaken until the ICP returns to the acceptable range. Alternatively, as will be discussed below, brain activity may be monitored and the conclusions concerning the level of ICP and actions to be taken may be made based on analysis of the brain activity detected. For example, data corresponding to the ICP may be generated by evoking and analyzing brainstem auditory responses (BAER) as described in U.S. Pat. No. 4,705,049 ("the '049 patent) the entire disclosure of which is hereby expressly incorporated by reference herein.

Figure 1A:
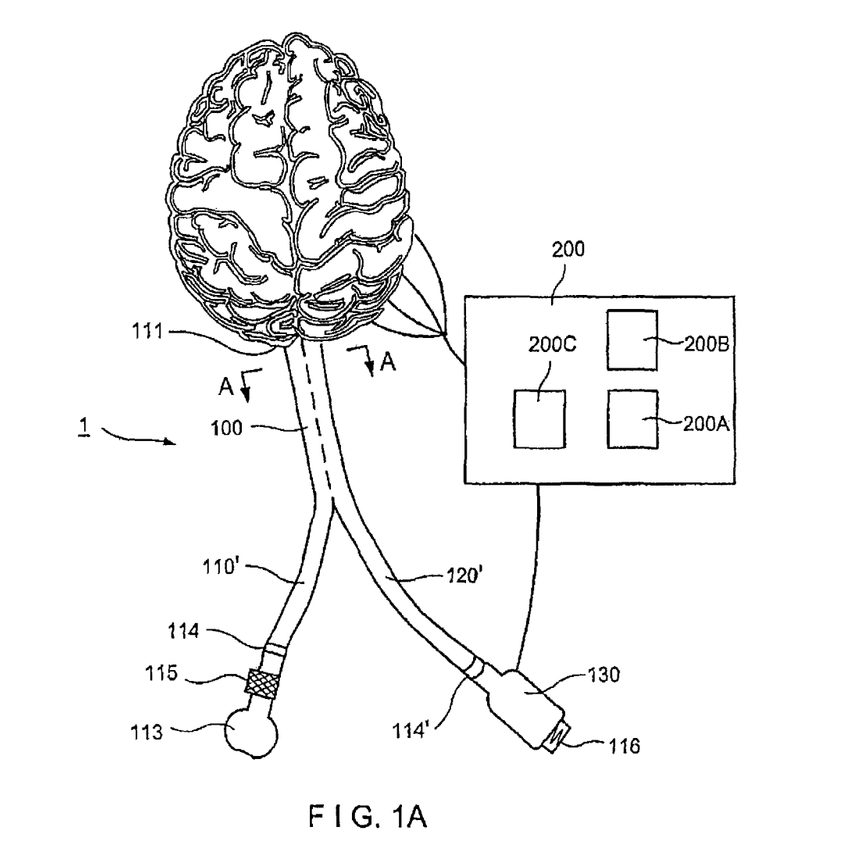
FIG. 1A shows an exemplary embodiment of a catheter assembly according to the present invention.
Figure 1B:
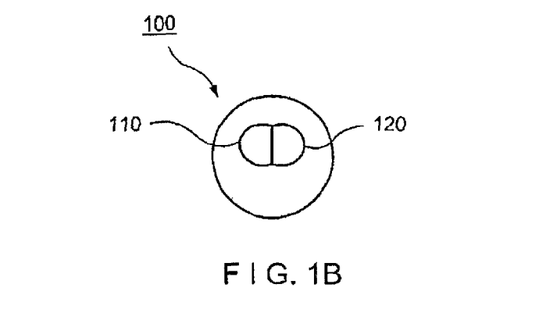
FIG. 1B shows a cross-section of the catheter assembly of FIG. 1A taken along line A-A of FIG. 1A.
Figure 2A:
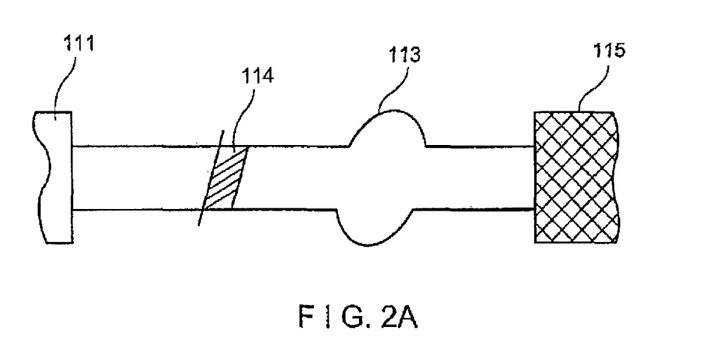
FIG. 2A shows an exemplary embodiment of a first branch of the catheter assembly of FIG. 1A.
Figure 2B:
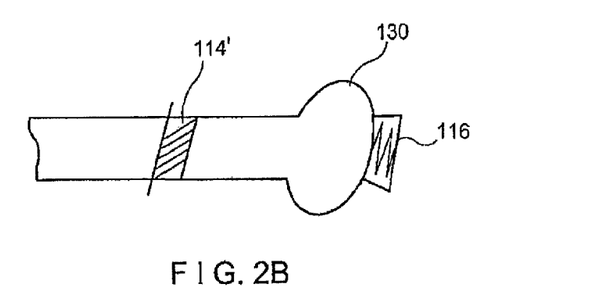
FIG. 2B shows a second branch of a catheter assembly according to an exemplary embodiment of the present invention.

FIGS. 1A and 1B show an exemplary embodiment of a catheter assembly 1 according to the present invention. The catheter assembly 1 includes a dual lumen catheter 100 and a data processing unit 200 which may include either or both of a QEEG monitor and a BAER monitor receiving data from electrodes placed on the scalp or under the skin as would be understood by those skilled in the art. As would be understood, the components of the catheter assembly 1 may be made from any bio-compatible materials, such as, for example, silicon. As shown in FIG. 1B, a distal end of a catheter 100 which comprises a first lumen 110 and a second lumen 120 is inserted into a ventricle of a patient's brain as discussed in more detail below. At some point along the length thereof, the first and second lumens 110, 120, respectively, of the catheter 100 divert into separate branches 110' and 120'. Alternatively, as would be understood by those of skill in the art, two single lumen catheters may be substituted for the catheter 100 with a first one of the catheters performing the same functions as the first lumen 110, and a second one of the catheters performing the same functions as the second lumen 120. As shown in FIG. 2A, the first lumen 110 extends past a valve 114 to a reservoir 113 which is coupled to a pump 115 so that fluids and/or therapeutic agents stored in the reservoir 113 may be fed through the first lumen to be supplied to the CSF. As shown in FIG. 2B, the proximal end of the branch 120' is coupled via a valve 114' to a receiving volume 130 and a relief valve 116 controls drainage of the fluid within the receiving volume 130 into the body. Exemplary internal locations for the receiving volume 130 include the venous system, peritoneal cavity, pleural cavity, etc., and an exemplary external location may include a drainage bag. The valve 114 acts as a check valve to prevent a back-flow of CSF from the CNS into the pump 115 and the valve 114' acts to prevent the flow of CSF into the receiving volume 130 to maintain a threshold pressure in the cranium. The valves 114 and 114' may, for example, be constructed as described in U.S. Pat. No. 3,985,140 to Harris, which is hereby expressly incorporated by reference herein. Alternatively, those skilled in the art will recognize that the valves 114, 114' may be any other flow control component which controls the flow of CSF therethrough so that flow is prevented or allowed only in amounts and directions and at times desired by the system. As would be understood by those skilled in the art, the pump 115 may be an osmotic pump, micromechanical pump, or other conventional pump.

Alternatively, fluid may be drained into the patient's body. In this case, the second lumen 120 may include a plurality of small holes in the distal end thereof, distal of the valve 114', so that CSF accumulating in the ventricle may enter the holes and drain from the catheter 100. In addition, a second pump (not shown) may be coupled to the second lumen 120 to assist in drawing CSF from the CNS. The second lumen 120 allows CSF to be withdrawn from the cranium, to remove accumulated, undesirable toxic substances and/or to enable microassays of a withdrawn CSF sample. Furthermore, as would be understood by those skilled in the art, a microassay or liquid chromatography chip or other suitable sensor differentially sensitive to specific substances may automatically regularly or continuously sense concentrations of these specific substances (e.g., in the receiving volume 130) and compare these concentrations to optimal amounts. The results of these comparisons may then be outputted to a clinician or may be sent directly to the data processing unit 200, described in more detail below, to modify the output of the pump 115. The CSF may be extracted from the receiving volume 130 for an external assay by puncturing the reservoir with a needle and withdrawing the sample therefrom into a syringe. As would be understood by those skilled in the art, in such an arrangement the needle would be inserted into a self-sealing septum so that, upon withdrawal of the needle leakage from the receiving volume 130 would be prevented.

As mentioned above, a withdrawn CSF sample may be microassayed to make adjustments and/or updates to balances of chemicals to be supplied to the CSF (e.g., by altering the make-up of the fluid included in the reservoir 113). If, upon assay of the withdrawn CSF sample, the CSF is found to contain undesirable material, it may be eliminated either spontaneously by withdrawing a quantity of the tainted CSF to spur the secretion of new CSF by the brain, or forcibly by the introduction of fluids via the first lumen 110 as described above. Furthermore, if microassay of the withdrawn CSF sample reveals excess or deficient electrolytes or the precursors or metabolites of cerebral neurotransmitters, the first lumen 110 may be used to infuse electrolytes or agonists or antagonists of the deviant neurotransmitter or any other agent in order to restore a desired balance.

The removal of CSF, and thus, toxic substances contained therein via the second lumen 120 prevents these toxic substances from being reabsorbed and recirculated and makes it possible to manage levels of these toxins. In addition, since the removal rate of these toxins may be equal to, if not higher than, their production rates, newly produced, clean CSF will displace the contaminated fluid. Thus, a transport rate of the CSF may be set at an optimum level to achieve and maintain a desired CSF composition. Those skilled in the art will understand that, CSF production varies significantly from patient to patient and, consequently, that the optimum transport levels will need to be varied as well to accommodate these differences.

In certain respects, the catheter 100 acts as a shunt system as described, for example, in U.S. Pat. No. 3,654,932 to Newkirk, et al., the disclosure of which is hereby incorporated by reference in its entirety. The catheter assembly 1 is introduced into the ventricular system of the brain, preferably into the third ventricle, through conventional surgery or any known technique as is done, for example, to regulate excess CSF in patients afflicted with hydrocephalus. For example, the catheter assembly 1 may be inserted through a burr hole of the skull and through the brain tissue, using a technique such as, for example, the one described in U.S. Pat. No. 5,312,357 to Buijs et al., the disclosure of which is hereby incorporated by reference in its entirety. The proximal end of the first lumen 110 may be inserted, e.g., into the patient's peritoneal cavity with the pump 115 and reservoir 113 in a position such that the reservoir 113 may be easily accessed in order to supply fluids and/or therapeutic agents thereto. As is generally done with ventricular shunts, the catheter assembly 1 may ultimately be covered and held in place by the scalp.

Figure 3:
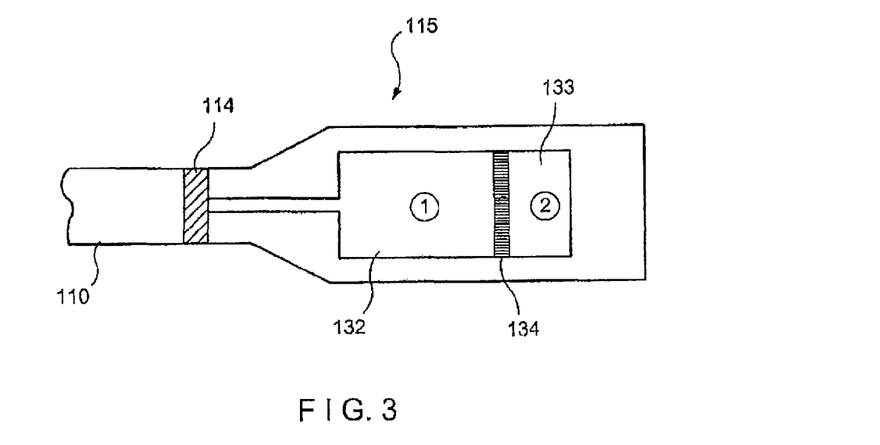
FIG. 3 shows an osmotic pump assembly for use in accord with the embodiment of FIG. 1A.

FIG. 3 shows in more detail an osmotic pump assembly (such as, for example, described in U.S. Pat. No. 6,436,091 to Harper et al.) which may be employed as the osmotic pump 115 of FIG. 2A. The osmotic pump assembly 115 comprises an osmotic reservoir 133 and an agent supply reservoir 132. The osmotic pump assembly 115 supplies fluid from the agent supply reservoir 132 to the CNS via the valve 114 when a concentration difference between the agent supply reservoir 132 and the osmotic reservoir 133 causes solvent to migrate across a semi-permeable membrane 134 extending therebetween. The membrane 134 may be formed, for example, of cellulose acetate or other suitable material as would be understood by those of skill in the art. As discussed in more detail below, the osmotic pump 115 may be replaced by a multi-chambered osmotic pump which can supply a combination of therapeutic agents to the CSF.

As would also be understood by those skilled in the art, the valves 114, 114' and/or the pump 115 may be activated to maintain a desired ICP based on feedback from an indwelling pressure sensor. That is, the valve 114' may be operated to allow CSF to drain from the CNS when a detected ICP is above a predetermined threshold. Alternatively, the ICP data may be output to allow manual adjustment of the ICP. Also, instead of directly measuring the ICP, the data processing unit 200 may analyze brain activity data and generate data corresponding to the ICP. For example, the data processing unit 200 may control a transmitting unit to send out a trigger signal, collect BAER data, analyze a resulting waveshape by optimal digital filtering and perform automatic peak detection of the BAER waveshape. Then, an interval between first and fifth peaks of this waveshape is determined. If this interval is greater than a predetermined threshold length, it is determined that the ICP is not optimum and, either this data is outputted to enable manual ICP adjustment or the data processing unit 200 controls the system to drain CSF until the BAER data indicates that the ICP is within the acceptable range. For example, if the interval between the first and fifth peaks of the BAER waveshape is greater than 4.2 milliseconds, the system determines that the level of the ICP is excessive (e.g., ICP>than 7.0 Torre) and CSF may then be drained until the BAER data indicates that the TCP is <7.0 Torre (i.e., when the interval between the first and fifth peaks is equal to or less than 4.2 milliseconds). Of course, those skilled in the art will understand that BAER data may be combined with detected pressure values if desired. In addition, a pump connected to the second lumen 120 may be employed under control of the data processing unit 200 to aid in draining CSF while the pump 115 may be used to add fluid to the CNS if the ICP is lower than a lower limit of the acceptable range.

In addition to the dual lumen catheter 100 and its components, as described above the system data processing unit 200 may comprise a QEEG and/or BAER unit or other sensory evoked potential system, as shown in FIG. 1A. As would be understood by those skilled in the art, the data processing unit 200 records and analyzes electrical activity of the brain through the use of a high-speed data processor and electrodes placed on or under the scalp and linked to the processor. The processor of the data processing unit 200 amplifies the detected electrical impulses of the brain and converts them into a wave pattern to provide biofeedback corresponding to brain activity. Alternatively, other known systems for detecting and analyzing brain activity may be used to monitor the same effects. The data processing unit 200 may be a conventional QEEG/BAER system utilizing electrodes removably attached to a patient's scalp and external data processing and monitoring equipment. Alternatively, the data processing unit 200 may be an implantable, fully internalized system directly linked to a central control unit which gathers data from the data processing unit 200 and from other sources and controls components of the system such as the osmotic pump 131 automatically to create a self regulating system. The electrodes for the data processing unit 200 system may, for example, be implanted in a manner similar to that described for the implantation of brain stimulating electrodes in U.S. Pat. No. 6,463,328 the entire disclosure of which is hereby expressly incorporated by reference herein.

More specifically, the data processing unit 200 may comprise a QEEG unit 200A, a BAER analyzer 200B and a transmitter 200C. The QEEG unit 200A preferably operates as would be understood by those skilled in the art to perform all the functions of known quantitative electro encephalographic systems while the BAER analyzer 200B operates in conjunction with the transmitter 200C to analyze BAER data evoked by auditory stimulus generated by the transmitter. For example, the transmitter 200C may send out a trigger signal, while the electrodes forward data to data processing unit 200. The BAER analyzer 200B then eliminates noise from the signal and analyzes the BAER waveshape by optimal digital filtering and performs automatic peak detection of the BAER waveshape to determine the interval between the first and fifth peaks. This data is then used by the data processing unit 200 to control the shunting of CSF to progressively adjust the ICP until the interval between the first and fifth peaks of the BAER waveform is no greater than a predetermined threshold value (e.g., 4.2 milliseconds) or until the ICP is below a predetermined threshold (e.g., 7.0 Torre).

The data processing unit 200 may be used to monitor the effects of the chemicals and CSF interventions created by the present invention. It may gauge the rate and amount of infusion required by evaluating the restoration of any deviant brain electrical parameters to control data corresponding to activity of the brain when symptoms of the CNS disorder are not present or to known normative values appropriate for the age, gender, etc, of the patient. Such age-appropriate normative data may, for example, be installed in a ROM unit of the data processing unit 200 prior to implantation. Alternatively, the data processing unit 200 may include an interface allowing for updated normative data to be provided thereto after implantation.

As described above, a plurality of electrodes coupled to the data processing unit 200 are coupled to a patient's scalp. In addition, the data processing unit 200 may be connected to the osmotic pump assembly 115 so that operation of the pump 115 may be controlled thereby based on the brain activity detected by the data processing unit 200. As would be understood by those of skill in the art, each of the plurality of electrodes is connected via a plurality of leads to the data processing unit 200 so that the data processing unit 200 acquires an EEG signal (i.e., brain-waves). The data processing unit 200 then analyzes and operates on this EEG signal using, for example, spectral analysis. The output from this EEG signal analysis is compared by the data processing unit 200 to reference data (e.g., normative values for the age of the patient or data from taken from this patient when no symptoms (or reduced symptoms) of the CNS disorder were present). This analysis is more fully described in the article John et al., "Neurometrics: Computer Assisted Differential Diagnosis of Brain Dysfunctions" Science 293:162-169, 1988 ("the Science Article"). The Science Article is hereby expressly incorporated into this application in its entirety by reference. The analysis may indicate a deviation from the nouns indicating that CSF should be drained or that therapeutic agents should be infused. If so, the data processing unit 200 may provide a signal to the osmotic pump assembly 115 or to the valve 114' directing changes required to restore any deviant brain electrical parameters indicated by the data analysis. For example, if the analysis indicates that a concentration of a particular chemical being supplied to the CSF is at a threshold level or higher than desired, the data processing unit 200 may notify the osmotic pump assembly 115 to reduce the rate of chemical infusion or stop it altogether until the detected brain activity indicates that the concentration of this chemical has dropped below the threshold value. Or, if the analysis indicates an excessive level of a toxin produced within the brain, the data processing unit 200 may direct the forcible introduction of fluids to reduce the toxin concentration, etc. Of course, those skilled in the art will understand that in any or all of the cases, the data processing unit 200 may provide output data to an operator of the system who can override any automatic controls which the data processing unit 200 may be preparing to enact. In addition, the data processing unit 200 may alert the operator or the patient whenever any of a plurality of predetermined conditions arises.

As described above, the data processing unit 200 is also connected to the valve 114' of the second lumen 120. After the EEG signal analysis has been conducted by the data processing unit 200 as described above, the data from the data processing unit 200 may be provided to an operator who may make adjustments as necessary. Alternatively, the data processing unit 200 directly control the valve 114' based on this data to either increase or decrease an amount of CSF being drained from the ventricle. Thus, the data processing unit 200 may regulate the drainage of CSF as well as the infusion of chemicals into the CSF.

Figure 4:
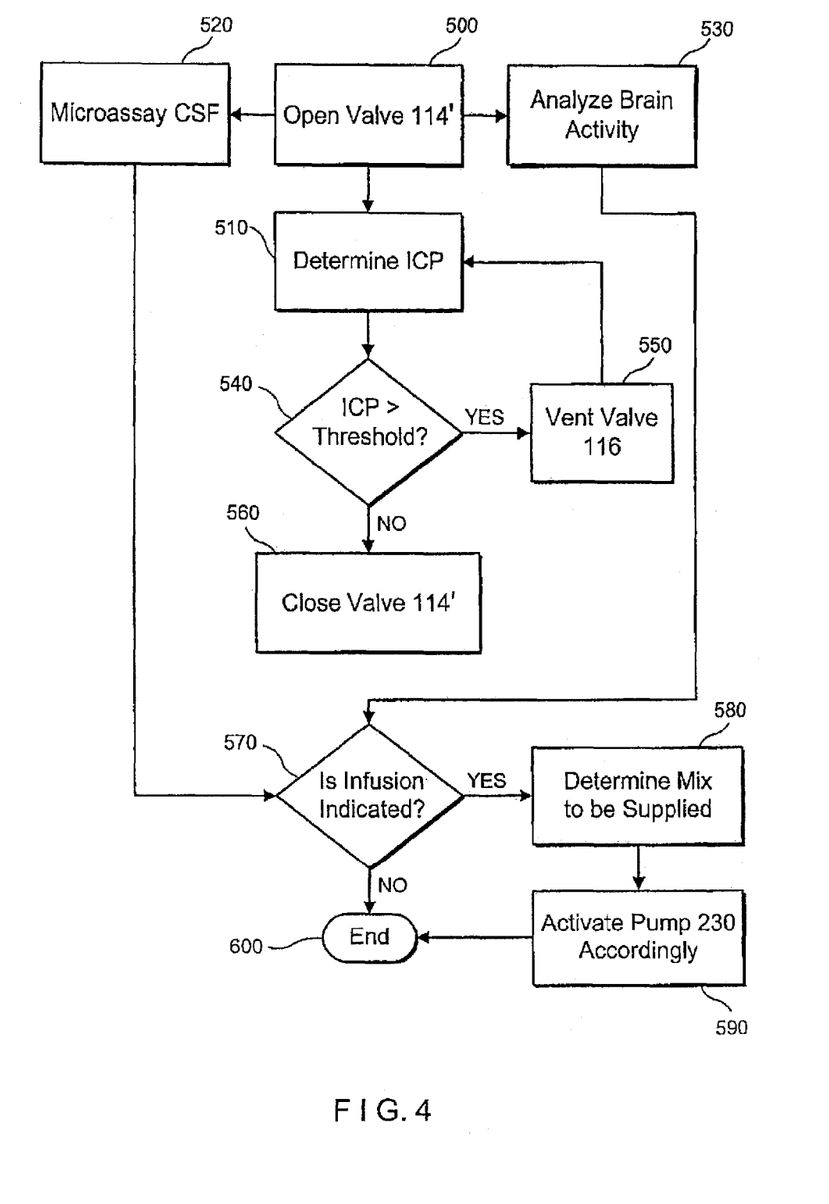
FIG. 4 shows an exemplary embodiment of a method for the correction of neurophysiological disequilibria in the central nervous system according to the present invention.

FIG. 4 shows an exemplary embodiment of a method for the correction of intracerebral chemical imbalances according to the present invention. Once the catheter assembly 1 has been inserted into the ventricle, CSF is drained through the second lumen 120 into the receiving volume 130 (step 500) by opening the valve 114'. At the same time, the data processing unit 200 then determines the ICP (step 510), microassays the fluid in the receiving volume 130 (step 520) and analyzes brain activity (step 530). Of course, those skilled in the art will understand that the removal and/or assay of CSF via the second lumen 120 may be ongoing simultaneously with the introduction of agents to the ventricle via the first lumen 110. Then, the ICP is compared to a predetermined threshold (step 540) and, if the ICP is greater than this amount, the valve 116 is opened to drain CSF from the CNS (step 550). If the ICP is less than the threshold amount, the valve 116 is maintained closed (step 560). Based on the analysis of brain activity in step 530 and the microassay of the CSF in step 520, the data processing unit 200 determines whether the infusion of fluids or therapeutic agents is indicated (step 570). If the infusion of fluids and/or therapeutic agents is indicated, the data processing unit 200 determines the desired mix of fluids and/or agents to be supplied (step 580). Then the data processing unit controls the pump 230 (described below) to supply the desired mix to the CNS (step 590). Those skilled in the art will understand that the data processing unit 200 may analyze brain activity continuously or at regular intervals with a delay factored in based on an expected time for the diffusion of therapeutic agents to the targeted areas in the brain and that the data may be interpreted by the data processing unit 200 as described, for example, in the Science Article.

Figure 5:
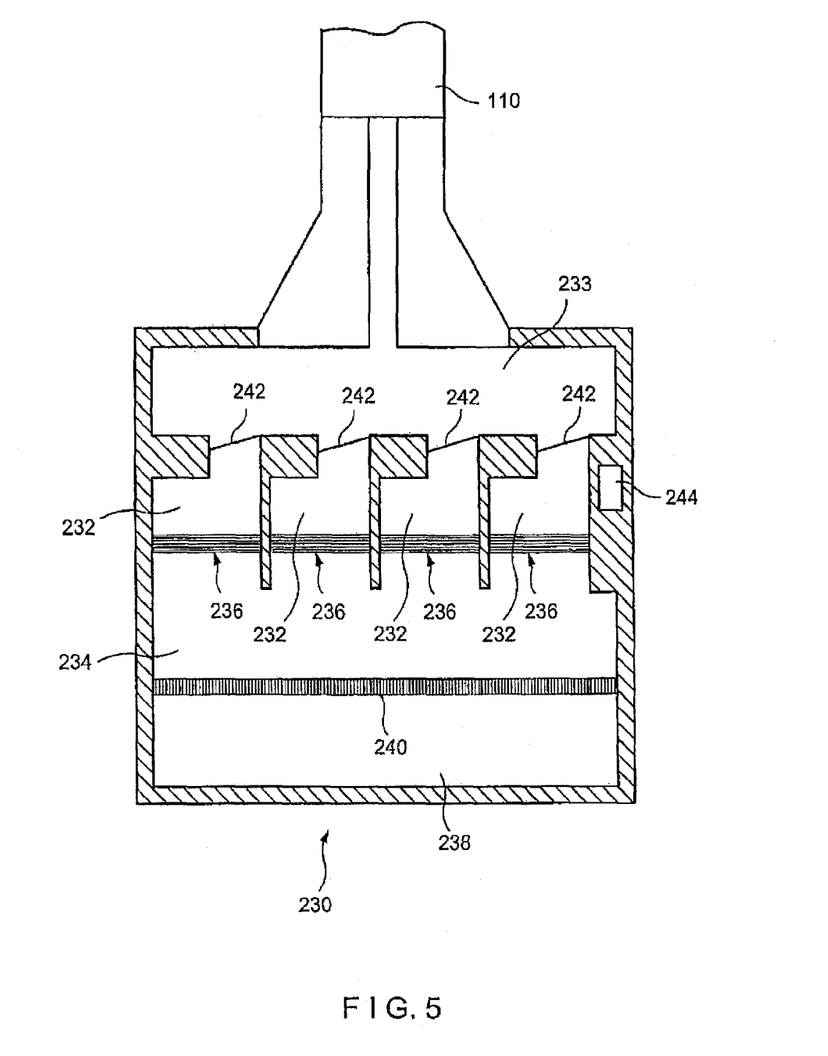
FIG. 5 shows a cross-sectional view of a multi-chamber osmotic pump according to an embodiment of the invention.

As shown in FIG. 5, a multi-chamber pump 230 which includes a plurality of chemical reserves 232 may be substituted for the pump 115 of FIG. 1A. Each of the chemical reserves 232 is separated from a first solute reservoir 234 by a corresponding flexible membrane 236. The first solute reservoir 234 is separated from a second solute reservoir 238 by a semi-permeable membrane 240 and each of the chemical reserves is separated from a mixing volume 233 in fluid communication with the first lumen 110 by a corresponding valve 242. Thus, when a concentration difference exists between the first and second solute reservoirs 234, 238, respectively, solvent migrates across the membrane 240 until the concentrations on either side thereof are balanced. For example, if the concentration of the solute is higher in the first solute reservoir 234 than in the second solute reservoir 238, solvent moves across the membrane 240 from the second solute reservoir 238 into the first solute reservoir 234 to balance the concentrations. The increased volume of solvent in the first solute reservoir 234 exerts pressure on the flexible membrane 236. However, the flexible membranes 236 can not be moved to expand this volume unless one or more of the valves 242 is moved to the open position. A valve control mechanism 244 operates to open a selected one or a selected plurality of the valves 242 so that the corresponding portion (or portions) of the flexible membrane 236 may be pushed into the respective chemical reserve(s) 232 to supply the chemical(s) stored therein to the CSF via the mixing volume 233 and the first lumen 110. Alternatively, each chemical may be stored in a separate chemical reserve and pumped from there into the CSF by a corresponding miniature piezo-electric or osmotic pump as would be understood by those skilled in the art.

Those skilled in the art will understand that the valve control mechanism 244 may be coupled to the data processing unit 200 for automatic control based on analysis of brain activity or, alternatively, may be controlled by an operator from outside the body using known magnetic switches, to achieve a desired balance of a plurality of therapeutic agents supplied to the CSF. In addition a valve may be placed between the mixing volume 233 and the first lumen 110 so that selected chemicals may be mixed within the mixing volume 233 before they are transported to the CSF via the first lumen 110.

There are many modifications of the present invention which will be apparent to those skilled in the art without departing form the teaching of the present invention. The embodiments disclosed herein are for illustrative purposes only and are not intended to describe the bounds of the present invention which is to be limited only by the scope of the claims appended hereto.

What is claimed is:

1. An osmotic pump, comprising:
a first agent reservoir;
a first solute chamber;
a first flexible membrane separating the first agent reservoir from the first solute chamber;
a first valve moveable between an open position in which the first agent reservoir is open to an outlet of the osmotic pump and a closed position in which the first agent reservoir is sealed with respect to the osmotic pump outlet; and
a valve control mechanism selectively moving the first valve between its open and closed position in response to an instruction received from a processor.

2. The osmotic pump of claim 1, wherein the processor is configured for automatic control based on an analysis of brain activity.

3. The osmotic pump of claim 1, wherein the processor is controlled by an operator from outside the body.

4. The osmotic pump of claim 1, wherein the valve control mechanism maintains a predetermined threshold pressure in a cranium.

5. The osmotic pump of claim 4, wherein the valve control mechanism is operably connected to a pressure sensor in the cranium.

6. The osmotic pump of claim 1, wherein, in the open position, the first flexible member deflects into the first agent reservoir to increase a volume of the first solute chamber.

7. The osmotic pump of claim 6, wherein the first flexible member is prevented from deflecting into the first agent reservoir unless the first valve is moved to the open position.

8. The osmotic pump of claim 1, further comprising:
a second agent reservoir; and
a second flexible membrane separating the second agent reservoir from the first solute chamber.

9. The osmotic pump of claim 8, further comprising a second valve moveable between an open position in which the second agent reservoir is open to an outlet of the osmotic pump and a closed position in which the second agent reservoir is sealed with respect to the osmotic pump outlet, wherein the valve control mechanism selectively moves the second valve between its open and closed position in response to an instruction received from the processor.

10. The osmotic pump of claim 9, further comprising a mixing chamber positioned between the first and second agent reservoirs and the osmotic pump outlet.

11. The osmotic pump of claim 10, further comprising a mixing chamber valve positioned between the mixing chamber and the osmotic pump outlet so that the first and second agents may be mixed within the mixing chamber before being discharged from the osmotic pump outlet.

12. The osmotic pump of claim 1, further comprising a second solute chamber.

13. The osmotic pump of claim 12, further comprising a semi-permeable membrane separating the first and second solute chambers from one another.

14. An osmotic pump, comprising:
a first agent reservoir housing a first agent;
a first solute chamber;
a first flexible membrane separating the first agent reservoir from the first solute chamber;
a mixing chamber;
a first valve separating the mixing chamber from the first agent reservoir, the first valve being movable between an open position in which the first agent reservoir is open to the mixing chamber and a closed position in which the first agent reservoir is sealed with respect to the mixing chamber;
a second valve separating the mixing chamber and an outlet of osmotic pump, the second valve being movable from an open position in which the mixing chamber is open to the outlet and a closed position in which the mixing chamber is sealed relative to the outlet; and
a valve control mechanism selectively moving the first valve between its open and closed position in response to an instruction received from a processor, wherein the processor is configured for one of automatic and manual control, the valve control mechanism maintaining a predetermined threshold pressure in a cranium.

15. The osmotic pump of claim 14, further comprising:
a second agent reservoir housing a second agent; and a second flexible membrane separating the second agent reservoir from the first solute chamber.

16. The osmotic pump of claim 15, further comprising a third valve separating the mixing chamber from the second agent reservoir, the third valve being movable between an open position in which the second agent reservoir is open to the mixing chamber and a closed position in which the second agent reservoir is sealed with respect to the mixing chamber.

17. The osmotic pump of claim 16, wherein the third valve is movable independently of the first valve.

18. The osmotic pump of claim 15, further comprising:
a second solute chamber; and
a semi-permeable membrane separating the first solute chamber from the second solute chamber.

19. The osmotic pump of claim 18, wherein the semi-permeable membrane selectively permits migration of the first and second solutes therethrough to balance a concentration thereof within the first and second solute chambers.

* * * * *